United States Patent [19]
Fergason

[11] Patent Number: 6,067,129
[45] Date of Patent: May 23, 2000

[54] WELDING LENS WITH INTEGRATED DISPLAY AND METHOD

[75] Inventor: John D. Fergason, Mountainview, Calif.

[73] Assignee: OSD Envizion, Inc., St. Louis, Mo.

[21] Appl. No.: 08/616,264

[22] Filed: Mar. 15, 1996

[51] Int. Cl.[7] ............................ G02F 1/133; G02F 1/1343
[52] U.S. Cl. ............................... 349/14; 349/77; 349/142; 2/8
[58] Field of Search .................................. 349/13, 77, 14, 349/74, 142, 139, 81, 75; 219/147, 2; 2/8, 431; 351/45 TD; 345/7; 250/205, 215, 229

[56] References Cited

U.S. PATENT DOCUMENTS

| | | |
|---|---|---|
| Re. 29,684 | 6/1978 | Gordon . |
| Re. 32,521 | 10/1987 | Fergason . |
| D. 349,588 | 8/1994 | Howard et al. . |
| D. 353,692 | 12/1994 | Fergason et al. . |
| 3,731,986 | 5/1973 | Fergason . |
| 3,881,809 | 5/1975 | Fergason et al. . |
| 4,039,254 | 8/1977 | Harsch . |
| 4,237,557 | 12/1980 | Gordon ...................................... 349/14 |
| 4,328,490 | 5/1982 | Usuba et al. ............................. 349/142 |
| 4,385,806 | 5/1983 | Fergason . |
| 4,436,376 | 3/1984 | Fergason . |
| 4,540,243 | 9/1985 | Fergason . |
| 4,582,396 | 4/1986 | Bos et al. . |
| 4,688,898 | 8/1987 | Oldendorf et al. ...................... 349/142 |
| 4,863,244 | 9/1989 | Fuerthlayer et al. ..................... 349/14 |
| 5,074,647 | 12/1991 | Fergason et al. . |
| 5,208,688 | 5/1993 | Fergason et al. . |
| 5,248,880 | 9/1993 | Fergason . |
| 5,252,817 | 10/1993 | Fergason et al. . |
| 5,347,383 | 9/1994 | Fergason . |
| 5,377,032 | 12/1994 | Fergason et al. . |
| 5,420,502 | 5/1995 | Schweitzer, Jr. .......................... 324/96 |
| 5,519,522 | 5/1996 | Fergason .................................. 349/14 |
| 5,671,035 | 9/1997 | Barnes ..................................... 351/45 |
| 5,751,258 | 5/1998 | Fergason et al. ......................... 349/16 |

*Primary Examiner*—William L. Sikes
*Assistant Examiner*—Tai V. Duong
*Attorney, Agent, or Firm*—Howell & Haferkamp, L.C

[57] ABSTRACT

An integral indicator or display for a welding lens, which has a twisted nematic liquid crystal cell light shutter, includes plural independently operable twisted nematic liquid crystal cell indicator portions integral with the light shutter twisted nematic liquid crystal cell, indicia associated with respective indicator portions to indicate an operating characteristic of the welding lens, circuitry for operating the lens and the indicator portions, and one or more switches for stepping the circuit through respective settings of operating characteristics, such as shade darkness, sensitivity and delay time. The indicator is dark when the light shutter is dark, and the light shutter may include in optical series with the twisted nematic liquid crystal cell, a birefringent liquid crystal cell light shutter which is faster acting than the twisted nematic liquid crystal cell and can be driven to various shades at respective speeds depending on applied electric field. A method of protecting the eyes of a welder includes selecting an operating characteristic of a welding lens and using a display portion of the welding lens to display an operating characteristics of the welding lens.

60 Claims, 3 Drawing Sheets

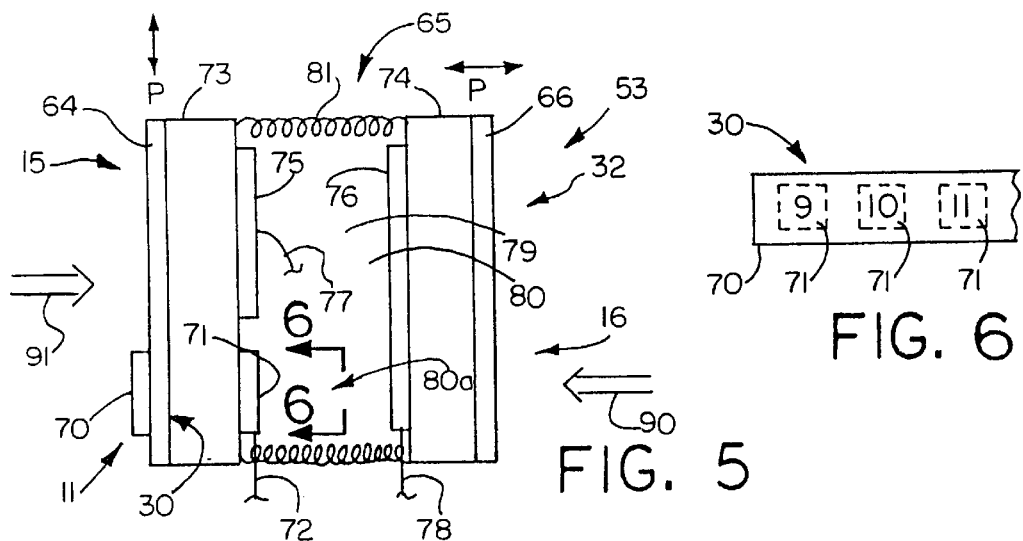
FIG. 5
FIG. 6
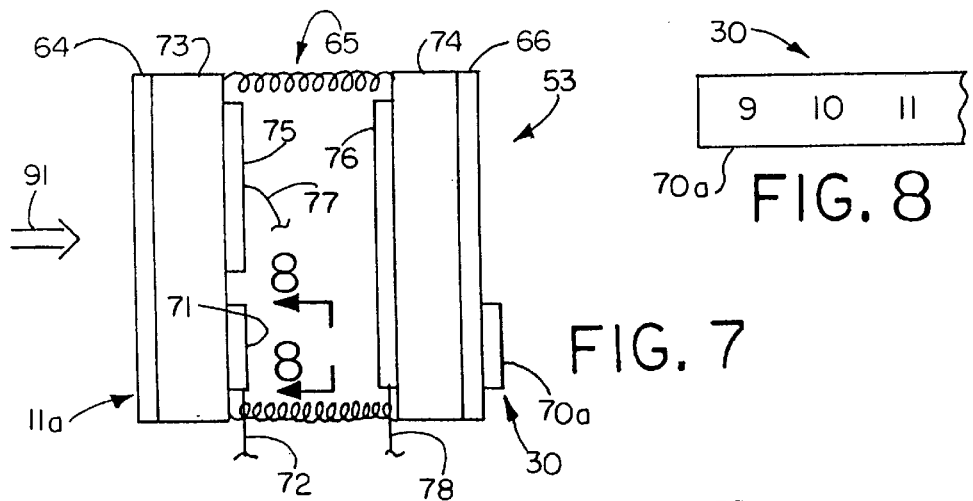
FIG. 7
FIG. 8
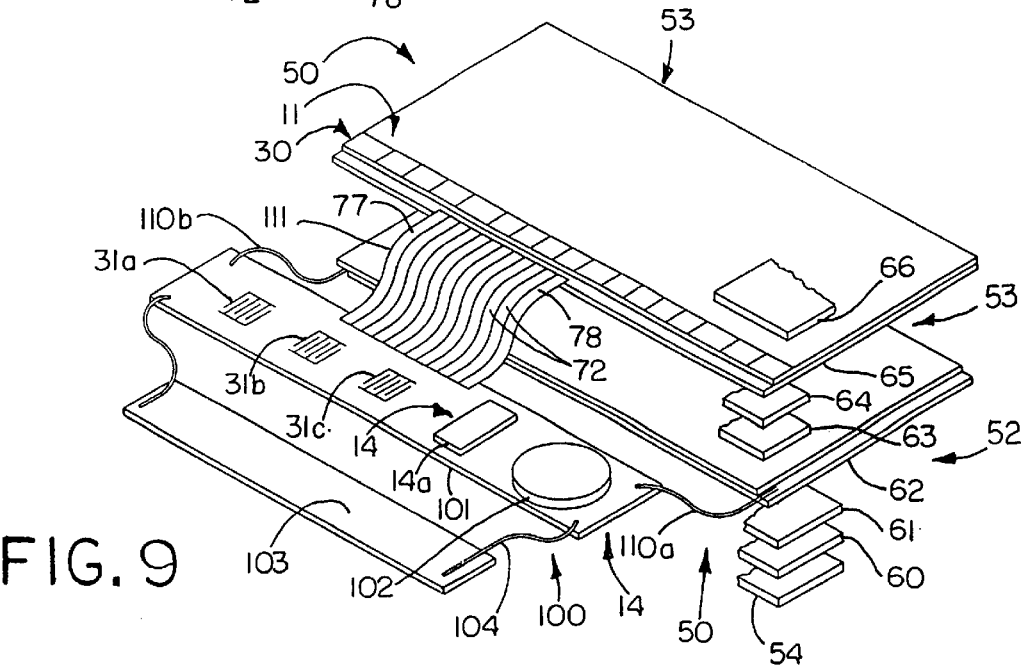
FIG. 9

WELDING LENS WITH INTEGRATED DISPLAY AND METHOD

TECHNICAL FIELD

The present invention relates generally, as is indicated, to an indicator system for a light shutter or the like, and, more particularly, to an automatic welding lens with an integral display or indicator to display various operative characteristics of the welding lens and to a method for protecting the eyes.

The present invention also relates generally to the control of transmission of electromagnetic energy, such as light in the visible, infrared and/or ultraviolet wavelength ranges, and, more particularly, the present invention relates to improvements for displaying the operative mode of an automatically controlled eye protection device, such as a welding helmet or lens for a welding helmet or the like.

BACKGROUND

In the following description reference will be made to a lens, especially to an automatically darkening lens that is able to operate automatically to control transmission of light. The lens may be a light shutter type of a device that is able to control light transmission without distorting, or at least with relatively minimal distortion, of the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, face masks, other types of helmets, etc. Such devices usually are employed to protect the face or the eyes of a person, as is known, for example, in the field of welding and in other fields, too.

For the purposes of providing eye protection, usually a welding lens provides light blocking characteristics in the visible, infrared and ultraviolet wavelength ranges. The actual ranges may be determined by the components of the lens, the arrangement of those components, and so forth. One example of a lens useful in accordance with the present invention is disclosed in copending, commonly owned U.S. patent application Ser. No. 08/105,734, filed Aug. 11, 1993, the entire disclosure of which hereby is incorporated by reference. The lens assembly disclosed in that patent application includes several liquid crystal cell light shutters, several plane polarizers, and a reflector or band pass filter, which is able to reflect ultraviolet and infrared electromagnetic energy and possibly also some electromagnetic energy in the visible wavelength range. The several liquid crystal cells, for example, may be birefringent liquid crystal cells sometimes referred to as surface mode liquid crystal cells or pi-cells.

Examples of liquid crystal cells, lenses using them and drive circuits are described in U.S. Pat. Nos. 5,208,688, 5,252,817, 5,248,880, 5,347,383, and 5,074,647 and in pending U.S. patent application Ser. No. 08/027,385 filed Feb. 17, 1993. In U.S. Pat. No. 5,074,647, several different types of variable polarizer liquid crystal devices are disclosed. Twisted nematic liquid crystal cells used in an automatic shutter for welding helmets are disclosed in U.S. Pat. Nos. 4,039,254 and Re. U.S. Pat. No. 29,684. Exemplary birefringent liquid crystal cells useful as light shutters in the present invention are disclosed in U.S. Pat. Nos. 4,385,806, 4,436,376, 4,540,243, 4,582,396, and Re. U.S. Pat. No. 32,521 and exemplary twisted nematic liquid crystal cells and displays are disclosed in U.S. Pat. Nos. 3,731, 986 and 3,881,809. The entire disclosures of the patents and applications mentioned herein are incorporated by reference.

As is disclosed in several of the above patents, the respective shutters may have one or more operational characteristics (sometimes referred to as modes or states). One example of such an operational characteristic is the shade number; this is the darkness level or value of the shutter when it is in the light blocking mode. Another exemplary operational characteristic is the delay time during which the shutter remains in a dark state after a condition calling for the dark state, such as detection of the bright light occurring during welding, has ceased or detection thereof has terminated or been interrupted. Still another operational characteristic is sensitivity of the detection circuit and/or shutter to incident light, for example, to distinguish between ambient conditions and the bright light condition occurring during a welding operation. Even another characteristic, which may be considered an operational characteristic, is the condition of the battery or other power source for the shutter, such as the amount of power remaining, operational time remaining until the power source becomes ineffective, etc. In the past various of the operational characteristics of such shutters have been adjustable or fixed. However, relatively large devices were used to adjust and to display the values or settings of such operational characteristics, as by dials or knobs. It would be desirable to reduce the space required for such components and to improve the operability of them. It would be desirable to minimize the size and weight of such control and display components thereby to minimize size and weight of a welding lens or other automatic shutter device. Further, it would be desirable to facilitate manufacturing such automatic shutters.

SUMMARY

With the foregoing in mind, then, one aspect of the present invention relates to a new indicator arrangement (sometimes referred to as a display) for a light shutter or the like wherein the indicator is integral with the shutter for indicating an operational characteristic thereof.

Another aspect of the invention relates to an improved indicator arrangement for a light shutter, such as a liquid crystal shutter.

Another aspect relates to an improved method for displaying one or more operational characteristics of a light shutter wherein an indicator is integral with the shutter.

A further aspect relates to a method for manufacturing a light shutter by including an integral indicator to indicate an operational characteristic of the shutter.

Another aspect relates to an improved indicator integral with a liquid crystal shutter and a circuit associated with the liquid crystal shutter for controlling the shutter and adjusting one or more operational characteristics thereof and wherein the indicator displays such characteristics.

Another aspect relates to the reducing of size requirements for a control circuit for operational characteristics of a liquid crystal shutter and an indicator system to indicate the operational characteristics thereof.

Another aspect of the invention relates to a light transmission controlling device including a liquid crystal shutter selectively operable to effect optical polarization and thereby to control transmission of light, and an indicator integral with the shutter for indicating an operational characteristic thereof.

Another aspect relates to a light shutter having at least respective relatively dark and relatively clear states including a light control device controllable to switch between respective relatively clear and dark states, a circuit having respective operating modes for controlling operation of the light control device, and an indicator on the light control device and responsive to the circuit for indicating the operating modes.

Another aspect relates to an automatic welding lens system including an input polarizer, a first light shutter operable selectively to affect polarization of incident polarized light, a first analyzer for transmitting or blocking light from the first light shutter depending on the polarization thereof, a second light shutter operable selectively to affect polarization of incident polarized light from the first analyzer, a second analyzer for transmitting or blocking light from the second light shutter depending the on the polarization thereof, and an indicator integral with one of the light shutters for indicating an operational characteristic thereof.

Another aspect relates to a liquid crystal optical device including a light shutter for selectively controlling light transmission to a viewing area, the light shutter including a pair of substrates, liquid crystal material between the respective substrates, the liquid crystal material being functional selectively to affect optical polarization characteristic of polarized light, electrodes associated with the respective substrates for selectively applying electric field to liquid crystal material therebetween to change the characteristics of light transmission through a viewing portion of the light shutter, and at least one of the electrodes including an electrode portion that is separately operable from another portion thereof for selective operation to display for viewing indicia representative of a characteristic of the light shutter.

Another aspect relates to a welding helmet including a liquid crystal optical device comprising a light shutter for selectively controlling light transmission to a viewing area, the light shutter including a pair of substrates, liquid crystal material between the respective substrates, the liquid crystal material being functional selectively to affect optical polarization characteristic of polarized light, electrodes associated with respective substrates for selectively applying electric field to a liquid crystal material therebetween to change the characteristics of light transmission through a viewing portion of the light shutter, at least one of the electrodes including an electrode portion that is separately operable from another portion thereof for selective operation to display for viewing indicia representative of a characteristic of the light shutter; a housing for holding therein respective portions of the shutter device and a face shield in which the housing is mounted.

Another aspect relates to a method of protecting the eyes of a welder using an automatic darkening welding lens assembly including selecting an operating characteristic of the welding lens assembly, using a display portion of the, welding lens assembly displaying such operating characteristic, placing a viewing portion of the welding lens assembly before the eyes of the welder to provide a light shuttering operation for eye protection, and darkening the display portion of the welding lens assembly when the viewing portion has darkened to protect the eyes of the welder.

Another aspect relates to an automatic darkening welding lens assembly in which an indicator is integral with the welding lens assembly and is viewable when the welding lens assembly is not in the dark protective mode and is not viewable and does not interfere with eye protection when the welding lens assembly is in dark mode.

These and other objects, features, advantages and functions of the invention will become more apparent as the following description proceeds.

It will be appreciated that although the invention is described with respect to a preferred embodiment, the scope of the invention is limited only by the claims and equivalents thereof. Also, although the invention is described with respect to a liquid crystal light shutter used in a welding helmet for eye protection therein, it will be appreciated that the various features of the invention may be used in conjunction with other devices and functions.

To the accomplishment of the foregoing and related ends, the invention, then, comprises the features hereinafter described in the specification and particularly pointed out in the claims, the following description and the annexed drawings setting forth in detail certain illustrative embodiments of the invention, these being indicative, however, of but several of the various ways in which the principles of the invention may be suitably employed.

BRIEF DESCRIPTION OF THE DRAWINGS

FIG. 5 is a fragmentary side elevation view of one of the liquid crystal light shutters of the welding lens of FIG. 4 including an integral reflective indicator;

FIG. 6 is a back elevation view of the shutter indicia looking generally in the direction of the arrows 6—6 of FIG. 5;

FIG. 7 is a fragmentary side elevation view of one of the liquid crystal shutters of the welding lens of FIG. 4 including an integral transmissive indicator;

FIG. 8 is a back elevation view of the indicia looking in the direction of the arrows 8—8 of FIG. 7; and FIG. 9 is a fragmentary isometric view of the welding lens assembly of FIG. 4 including the associated drive circuitry.

DESCRIPTION

Figure 1:
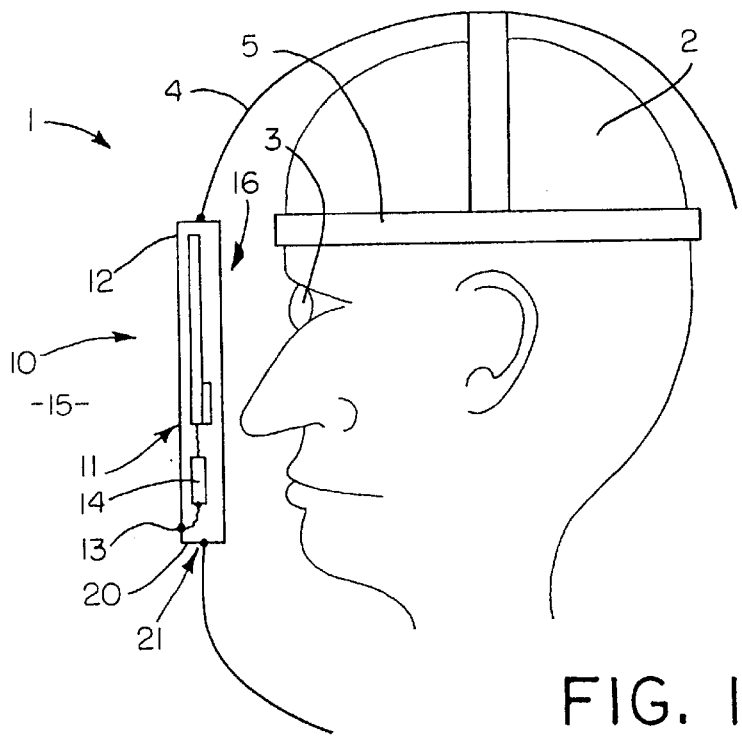
FIG. 1 is a schematic illustration of a welding helmet including a welding lens assembly with an automatic shutter and an integral indicator or display, the helmet being positioned on the head of an individual, such as a welder.

Referring in detail to the drawings, wherein like reference numerals designate like parts in the several figures, and initially to FIG. 1, there is illustrated a welding helmet 1 worn on the head of a person 2 to protect the person's eyes 3 from light generated during welding operation or some other operation in which eye protection from bright light is desired. The welding helmet 1 includes a shell 4, which provides physical protection for the person 2 from sparks, molten metal, small scattering debris, and the like, and a head gear 5, such as a mounting band or the like, for mounting the helmet on the head of the person 2. The welding helmet 1 may be a separate device or it may be part of a further assembly, such as a structure that provides air for breathing by the person 2, other ventilating equipment, etc.

To permit viewing by the person's eyes 3, when the welding helmet 1 is worn, the welding helmet 1 includes an automatic light shutter 10. An integral indicator 11 associated with the shutter 10 displays operative conditions of the shutter. The shutter and indicator are supported in a welding lens cartridge assembly 12 that is secured in the shell 4.

The shutter 10 is an automatic shutter able to be operated in a clear state or a dark state (and possibly also in one or more intermediate states) in response to lighting conditions detected by a sensor 13 which is coupled to operating or driving circuitry 14. In the embodiment described herein the shutter 10 includes plural liquid crystal cells which are operated by the circuitry 14 so that the shutter 10 selectively assumes the clear or light transmitting state or assumes the dark or light blocking state, depending on conditions detected by the sensor 13 and operation of the circuitry 14. Shutters, sensors and circuitry generally of the type described herein also are described in various of the above patents and applications.

In the clear state the shutter 10 transmits to the eyes 3 a relative maximum amount of light from outside the helmet to permit viewing of a welding location, tools for use in welding, a part being welding, etc. Being able to view the welding site, for example, facilitates the setting up of the welding tools so that the person can commence welding in an efficient and safe manner. When the sensor 13 detects the commencing of welding, the sensor output causes the circuitry 14 to drive the shutter 10 to the dark state blocking a substantial amount of light transmission from reaching the eyes 3 and, thus, providing eye protection. The light being blocked may be visible light, infrared light, and/or ultraviolet light. Reference to light herein means electromagnetic energy in the respective wavelength ranges indicated. Thus, in response to the occurrence of a specified light condition at the front or outside 15 of the welding lens cartridge assembly 12, the shutter 10, sensor 13 and circuitry 14 cooperate to protect the eyes 3 at the back 16 of the assembly 12 inside the helmet 1.

Figure 2:
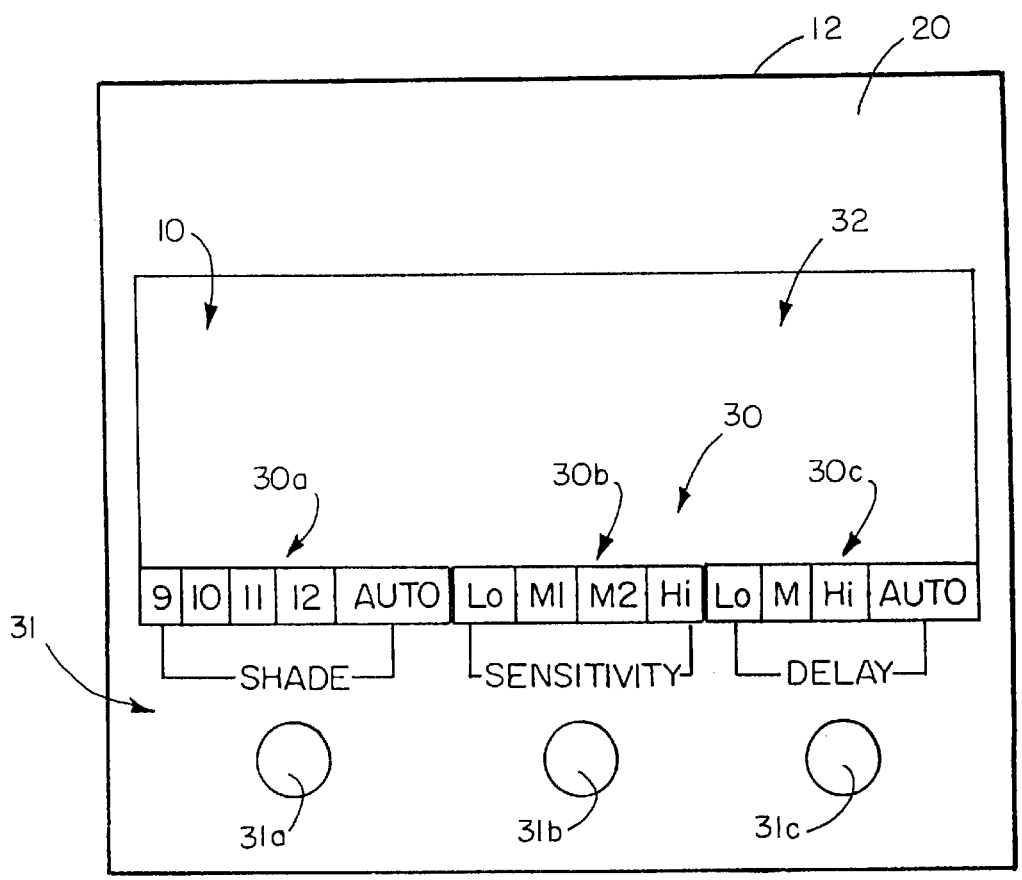
FIG. 2 is a back elevation view of the welding lens cartridge assembly of the welding helmet in FIG. 1.

Briefly referring to FIG. 2, the back side 16 of the welding lens cartridge assembly 12 is illustrated. The shutter 10 is mounted in a housing 20 of the assembly 12. The housing may be plastic, metal or some other material that provides suitable support structure for the lens holding it in place and also providing suitable mounting or connection in an opening 21 (FIG. 1) in the welding helmet shell 4. When the shutter 10 is in the clear state, a person can see directly through the shutter to view the environment external of the welding helmet 1. However, when the shutter 10 is in the dark state, preferably light transmission is blocked substantially, and easy viewing is limited to very bright areas, such as the area in close proximity to the place where welding is occurring and welding light is being developed. Preferably the welding helmet shell 4 and the cartridge assembly housing 20 are relatively non-transparent, most preferably not transparent at all, to block light transmission. Therefore, the only light received by the eyes 3 would be that passing through the shutter 10.

In FIG. 2 at the bottom of the shutter 10 is illustrated plural indicia 30 of the integral indicator 11 (FIG. 1). The indicia 30 are arranged in three groups 30a, 30b, and 30c, each group representing respective values or functions of operating characteristics of the shutter 10 and circuitry 14. For example, the indicia 30a are labeled respectively 9 through 12 and "Auto". The numerical values identify respective shade numbers, which represent respective dark states of the shutter. When the shutter 10 and circuitry 14 are set to operate at shade 9, which is a known light transmission value, then in the dark state the shutter 10 assumes a light blocking/transmitting characteristic of a shade 9 lens. Each of the shades 9 through 12 can be set for the shutter 10 by stepping the circuitry 14 in response to sequential operation of one of the switches 31, say switch 31a. For example, for a given shade number level, the circuitry 14 would be adjusted to apply a particular voltage to respective electrodes of liquid crystal cells included in the shutter to apply an electric field of corresponding magnitude to the liquid crystal to obtain the desired shade number value. In the "Auto" shade operating characteristic, the circuitry 14 may adjust shade depending on one or more other characteristics, such as a comparison between ambient brightness and brightness of light emitted during welding, specific ambient light conditions, etc. In operation of the integral indicator 11, only one of the respective indicia 30a would be visible at a particular time to indicate the particular shade operating characteristic of the shutter 10 as set in the circuitry 14 by appropriate operation of the switch 31a.

Similarly, switches 31b, 31c can be operated to sequence the circuitry 14 through respective sensitivity adjustments and through respective delay adjustments. The sensitivity adjustments include a low sensitivity, high sensitivity, and two intermediate sensitivity levels. Sensitivity is the responsiveness of the circuit to a change in light conditions detected by the sensor 13 so as to cause the circuitry to operate the shutter 10 from dark condition. The delay switch 31c may be operated to step the circuitry 14 15 sequentially through low, medium, high and automatic delay operational characteristics for the shutter 10. When the delay is low, the circuitry 14 operates the shutter 10 to dark to clear state relatively promptly after the cessation of welding has been detected by the sensor 13, and when the delay is high, that time period is longer. In the automatic delay mode, the circuitry 14 may determine automatically the delay period, for example, based on external conditions detected by the sensor 13, such as ambient lighting conditions, brightness of the welding light, a comparison thereof, etc.

Figure 3:
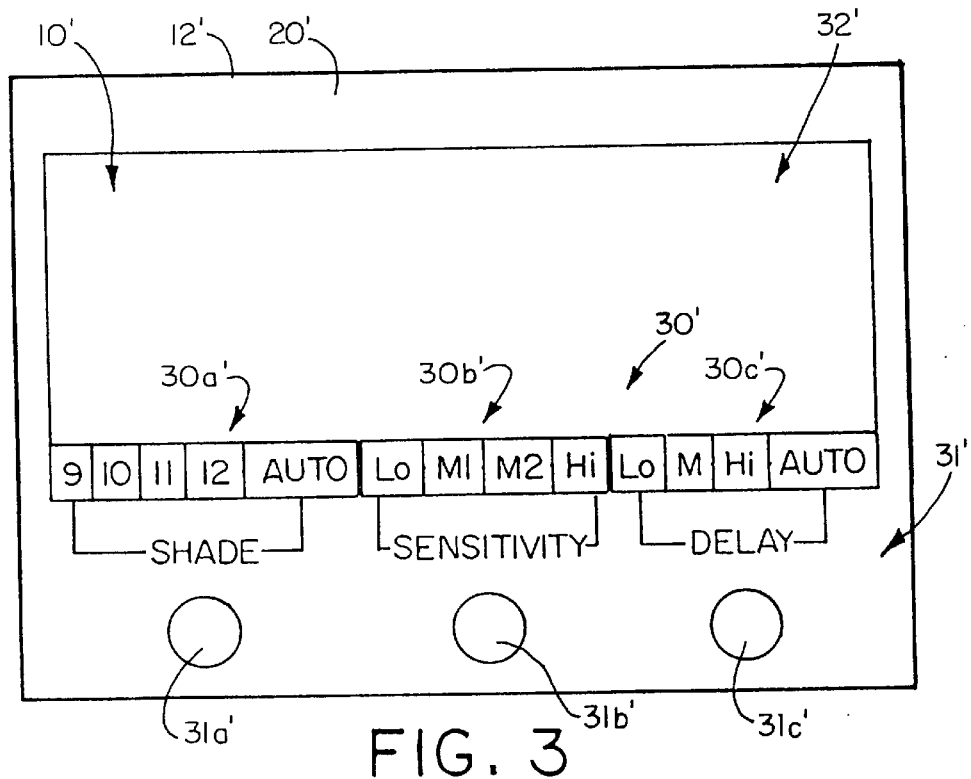
FIG. 3 is a back elevation view of an alternate embodiment of welding lens cartridge assembly having a reduced height profile relative to that of FIG. 2.

In FIG. 3 is illustrated an alternate embodiment of welding lens cartridge assembly wherein the various parts which correspond to those in the embodiment of FIG. 2 are designated by the same reference numerals, but the reference numerals are primed. Thus, the welding lens cartridge assembly 12' includes a shutter 10' located in the housing 20', and respective indicia 30' form part of the integral indicator 11 (FIG. 1) to display operational characteristics. An advantage to the integral indicator 11 of the invention, which will be described further just below, is that it minimizes the space required to display operational characteristics of the shutter 10' and associated circuitry 14. Also, the space required for the circuitry 14 may be minimized relative to space required for circuitry in prior automatic shutters and welding lens assemblies. Accordingly, as is illustrated in FIG. 3, the welding lens cartridge assembly 12' is smaller and may be lighter in weight than the housing 20 of the welding lens cartridge assembly 12 (FIG. 2), but the viewing area is 32, 32' of the respective shutters 10, 10' may be the same.

Figure 4:
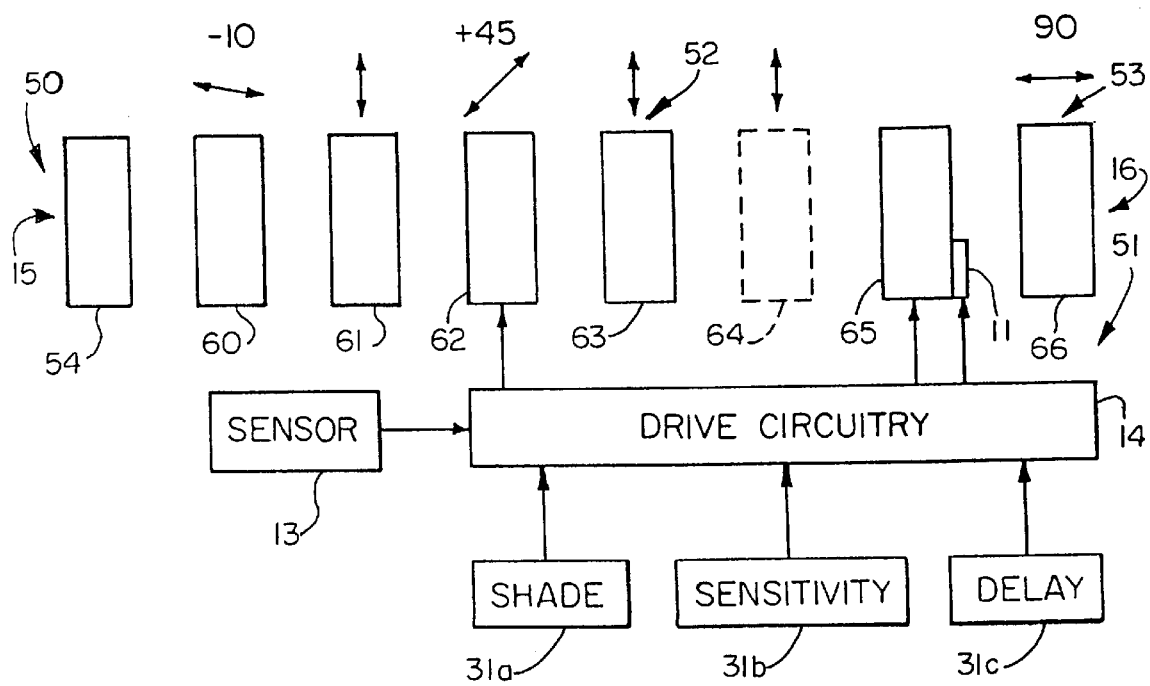
FIG. 4 is a schematic illustration of a series of optical components useful in the welding lens assembly of the invention.

Turning to FIG. 4, the shutter 10 with the integral indicator 11 and associated circuitry 14 are shown schematically in greater detail. Construction, use and operation of the shutter 10 is described with respect to protecting the eyes 3 during welding, and, therefore, the components of the shutter will be referred to below as a welding lens or simply as a lens, which is designated 50. However, the lens 50 and features thereof may be used for other eye protection, etc. purposes, and the integral indicator may be used in other devices, too. For convenience, the lens 50 in combination with the sensor 13, circuitry 14 and various adjustment controls, such as switches 31a, 31b, 31c, will be referred to here collectively as the welding lens assembly or simply as lens assembly 51. It will be appreciated that the components used in the lens assembly 51 are exemplary, and that other components may be used to provide a desired amount and type of optical protection, such as eye protection from bright light occurring in welding or in some other type of operation or as a result of some other type of phenomenon.

The integral indicator 11 is integral with a portion of the lens 50 and is operable to display to a user respective indicia 30 representing one or more operational characteristics of the lens assembly 51. In the embodiment described the indicator is near the bottom of the viewing area 32 of the lens 50. However, if desired, the indicator 11 may be positioned at another location in the lens 50. With the indicator 11 at or near the bottom of the lens 50, it will not interfere with (or at least it will only minimally interfere with) the viewing area 32 and field of view seen by the eyes 3 when the helmet 1 is worn (FIG. 1). However, the indicator 11 easily may be viewed when the helmet is not being worn and the lens 50 is not in the dark state. Additionally, as will become evident from the description below, the indicator 11 preferably does not interfere with the light blocking function of the lens 50.

The optical components of the welding lens 50, which are shown on FIG. 4, include a pair of liquid crystal shutters 52, 53 and input band pass filter 54. An additional output band pass filter or simply a protective transparent plate or filtering plate (not shown) may be provided at the front 15 or back 16 of the welding lens 50 for filtering function and/or for protection from damage, such as by scratching or the like.

The liquid crystal shutters 52, 53 and the band pass filter 54 are in optical series. The band pass filter 54 blocks from transmission to the liquid crystal shutters electromagnetic radiation (light) in the infrared and ultraviolet ranges. An exemplary band pass filter includes a hot mirror, such as that sold under the trademark Coolbeam™ wide band hot mirror by Optical Coating Laboratory, Inc. of Santa Rosa, Calif. with an additional coating of indium tin oxide to provide adequate filtering of infrared energy to 2,000 nm (nanometers). An example of such a band pass filter is described in copending, commonly assigned U.S. patent application Ser. No. 08/105,734, filed Aug. 11, 1993, now U.S. Pat. No. 5,519,552.

The first liquid crystal shutter 52 includes in optical series an input polarizer 60, a wave plate 61, a liquid crystal cell 62, and an output polarizer (sometimes referred to as an analyzer) 63. The polarizer 60 and analyzer 63 preferably are plane (linear) polarizers. The wave plate 61 may be a quarter wave plate for green light, although it may be a quarter wave plate for other than green light or for more than green light, and, if desired, the wave plate 61 may be other than a quarter wave plate. The liquid crystal cell 62 is a birefringent cell, such as a surface mode liquid crystal cell or pi-cell as is described in various of the aforementioned patents. The wave plate 61 compensates for residual retardation in the birefringent liquid crystal cell 62 as is described below. The alignment directions of the transmission axis for each polarizer 60, 63 and the axis of the wave plate 61 and the rub direction of the liquid crystal cell 62 are represented by arrows above the respective components.

The liquid crystal shutter 52 operates in response to voltage supplied by the drive circuitry 14. When the sensor 13 is not detecting welding and the drive circuitry 14 operates the liquid crystal cell 62 at relatively low voltage (for example, RMS voltage, DC or AC voltage), the liquid crystal cell provides optical phase retardation for incident polarized light to deliver as an output to the polarizer 63 light that is plane polarized substantially in the direction of the transmission axis of the polarizer 63. Therefore, the shutter 52 transmits a relatively maximum amount of light.

In contrast, when the sensor 13 is detecting welding and the drive circuitry 14 supplies a relatively high voltage to the liquid crystal cell 62, the amount of retardation provided by the liquid crystal cell is reduced so that the output provided the polarizer 63 is plane polarized light having an electric vector that is in a direction other than the direction of the transmission axis of the polarizer 63. In an embodiment of the invention, at maximum voltage provided by drive circuitry 14 to liquid crystal cell 62, the direction of plane polarized light output from the liquid crystal cell is substantially perpendicular to the direction of the polarizer 63 transmission axis. However, at a slightly reduced, but nevertheless relatively high, voltage, the direction of the plane polarized light remains substantially perpendicular or is only slightly deviating from perpendicular to the direction of the transmission axis of polarizer 63. As a result of such perpendicular or nearly perpendicular orientation of the polarized light incident on the polarizer 63, transmission thereof will be substantially blocked by the polarizer 63.

The liquid crystal shutter 52 is set up, i.e., the axial directions and respective values or parameters of the components 60–63 are so selected and arranged, that some light will be transmitted through the polarizer 63, even in the dark state, so that the person using the welding helmet 1 including the lens 50 will be able to see the welding operation while the eyes are protected from bright light. Also, as is known, most plane polarizers tend to leak some light, and such leakage by polarizer 60 of light that is not polarized in the direction of transmission axis thereof and leakage by polarizer 63 permits such transmission and viewing capability. However, the amount of light transmitted through the polarizer 63 when the lens 50 is in dark mode also can be adjusted by varying the voltage applied to the liquid crystal 62. By changing that voltage the amount of retardation applied to the light transmitted through the liquid crystal cell 62 can be changed, and, accordingly, the respective shade numbers identified by indicia 30a can be achieved by the welding lens 50.

Liquid crystal shutter 53 is in optical series with liquid crystal shutter 52 and band pass filter 54. Liquid crystal shutter 53 includes an input polarizer, which may be polarizer/analyzer 63 mentioned above or may be a separate polarizer 64, a liquid crystal cell 65, and an analyzer or output polarizer 66. Polarizers 64 and 66 are plane (linear) polarizers, and the relative directions of the transmission axes are identified by arrows above each polarizer. Although polarizer 64 may be optional, use may increase contrast ratio, improve efficiency and optimize performance of lens 50, especially if leakage light through polarizer 63 includes unpolarized light. Liquid crystal cell 65 is a twisted nematic liquid crystal cell. Such liquid crystal cell includes a pair of substrates on which electrodes are formed and between which nematic liquid crystal material is located. Absent a suitable electric field applied across a liquid crystal material by the electrodes, the liquid crystal material tends to rotate the plane of polarization of incident plane polarized light by an amount determined by the relative rub or alignment directions at the internal surfaces of the substrates; and in response to a suitable electric field, the liquid crystal material aligns with the field and transmits plane polarized light without altering (or substantially without altering) plane of polarization.

In operation of welding lens 50 in clear state, it is intended that a relatively maximum amount of light is transmitted to eyes 3. Accordingly, liquid crystal shutters 52, 53 transmit a relatively maximum amount of light. More specifically, band pass filter 54 performs its filtering function and transmits to input polarizer 60 at least some light that is in the visible wavelength range. Polarizer 60 polarizes that light and passes that plane polarized light to wave plate 61, and light from wave plate 61 is incident on birefringent liquid crystal cell 62. In clear state of lens 50, liquid crystal cell 62 provides maximum optical phase retardation and rotates plane of polarization of light incident thereon so that the plane of polarization is substantially parallel to the direction of the transmission axis of analyzer 63 for transmission thereby. Plane polarized light from polarizer 63 is directed to the second liquid crystal shutter 53. In the second liquid crystal shutter 53, plane polarized light from the analyzer 63 is transmitted directly to or via plane polarizer 64 to twisted nematic liquid crystal cell 65. If polarizer 64 is used, it serves as the input polarizer to liquid crystal shutter 53, and if not used, then the analyzer 63 serves as the input polarizer to the liquid crystal shutter 53. The liquid crystal cell 65 is in the twisted mode so that it rotates the plane of polarization of the incident light thereto to a direction that is parallel to the alignment direction of the transmission axis of the analyzer 66. Accordingly, the light is transmitted through the analyzer 66 as output light at the back 16 of the lens 50 for viewing by the eyes 3.

During operation of the welding lens 50 in the clear state, the drive circuitry 14 may operate the indicator 11 to present a display of respective indicia 30 for viewing by the user before placing the welding helmet on the head 2. While the indicia are displayed, the user may operate one or more of the respective switches 31$a$, 31$b$, 31$c$ (or other ones, if used) to set desired operational characteristics for the welding lens assembly 51. The indicator 11 may include transmissive or reflective display portions and which can be seen clearly when the lens 50 is in the clear state.

The birefringent liquid crystal cell 62 in the liquid crystal shutter 52 may have residual birefringence even when it is driven at maximum voltage. The wave plate 61 is provided in the liquid crystal shutter 52 to compensate for such residual birefringence, and the alignment of the transmission axis for the input polarizer 60 also is set to cooperate with the wave plate 61 and with the operating characteristics of the birefringent liquid crystal cell in the respective clear and dark states so that plane polarized light will be selectively transmitted or blocked by the polarizer 63 in response to the actual voltage or RMS voltage applied by the drive circuitry 14 and the corresponding electric field developed in the birefringent liquid crystal cell 62. Such compensation provided by the wave plate 61 and alignment of the input polarizer 60 are described in various of the aforementioned patents and patent applications, such as, for example, in the '688 patent.

In operation of welding lens 50 in dark state, upon welding or some other conditions occurs that is detected by the sensor 13 to cause a drive circuitry 14 to operate the welding lens 50 in the dark state, the following occurs. The drive circuitry 14 drives the liquid crystal shutters 52, 53 to the dark states. The birefringent liquid crystal cell 62 is driven at a relatively high voltage so that the liquid crystal material therein does not retard (or rotate) the polarized light transmitted therethrough, and with compensation provided by the wave plate 61 and the alignment of the input polarizer 60, the result is substantial blocking of light transmission by the analyzer 63. Polarized light transmitted by the polarizer 63 is delivered directly or via the polarizer 64 to the twisted nematic liquid crystal cell 65. The drive circuitry 14 also operates the twisted nematic liquid crystal cell 65 driving it to a state that it does not rotate plane of polarization. Therefore, the light incident on the analyzer 66 is plane polarized in the direction that is perpendicular to the direction of the transmission axis of such analyzer 66, and the analyzer 66 will block a substantial amount of such light.

The percentage of light blocked by the liquid crystal shutter 53 in the dark state ordinarily will remain relatively constant. However, the percentage of light blocked by the liquid crystal shutter 52 may be altered by changing the voltage applied to the liquid crystal shutter 62; such alteration allows the lens 50 to be operated at different respective shade numbers. Such shade numbers can be controlled by operating the switch 31$a$ to change operational characteristics of the circuitry 14, for example, by switching the values of various resistors in the circuit, etc. It will be appreciated that operation of the welding lens 50 to provide a relatively low shade number requires less voltage and power from the drive circuitry 14 and the power source therefor, and a higher shade number ordinarily will require a higher voltage and more power, for example, to drive the birefringent liquid crystal cell 62. The sensitivity and delay operating characteristics of the welding lens assembly 51 can be similarly adjusted by operating the switches 31$b$, 31$c$.

An advantage to the combination of a birefringent liquid crystal shutter 52 and a twisted nematic liquid crystal shutter 53 in optical series in the welding lens 50 is the complimentary response times and voltage requirements. For example, a twisted nematic liquid crystal shutter 53 ordinarily does not require power in the twisted state (in this case the clear state) and requires less voltage and power to operate it driving it to the "untwisted" and in this case, dark, state than the voltage requirements for a birefringent liquid crystal shutter. However, operation of the twisted nematic liquid crystal shutter ordinarily is slower than that of a birefringent liquid crystal shutter. Therefore, upon the occurrence of welding and detection of the welding light by the sensor 13, the drive circuitry 14 provides outputs to drive the liquid crystal cell 62, 65 to dark state. The birefringent liquid crystal cell takes more voltage and operates faster than the twisted nematic liquid crystal cell 65 and, therefore, promptly darkens the welding lens 50. If desired, the drive circuitry 14 may compensate for the slower operation of the twisted nematic liquid crystal cell 65. In such case the circuitry 14 initially supplies to the birefringent liquid crystal cell 62 a voltage larger than necessary to achieve the desired shade number for the lens 50 so that the liquid crystal shutter 52 switches to dark state very fast and provides acceptable prompt eye protection. However, after the twisted nematic liquid crystal cell 65 has achieved its dark state, the voltage to the birefringent liquid crystal cell 62 can be reduced so that the liquid crystal shutters 52, 53 operating an optical series provides a desired shade number and eye protection.

In FIGS. 5 and 6 is illustrated one embodiment of indicator 11 integral with the twisted nematic liquid crystal cell 65 of the liquid crystal shutter 53. The indicator 11 is a reflective type and it includes the indicia 30 printed on a reflective sheet or support 70. An example of a reflective support and display including a reflector is disclosed in U.S. Pat No. 3,881,809. In FIG. 6 three shade numbers of the indicia 30$a$ (FIG. 2) are depicted as examples; however, all of the indicia 30 may be printed on the support 70. The support 70 may extend across part or all of the width of the light shutter 65 preferably out of the viewing area 32. The indicator 11 also includes a plurality of transparent electrode segments 71, which are aligned in overlying relation to respective indicia, as is shown in FIG. 6. Each electrode segment 71 may be indium tin oxide or some other transparent electrode material, and each is connected by a respective lead, conductor or the like 72 to the drive circuitry 14 for selective energization (by application or not of a voltage) to cause viewing of a respective one of the indicia while light to others is blocked and they would not be seen.

Aside from the indicator 11, the liquid crystal cell 65 may be essentially a conventional twisted nematic liquid crystal cell. Such a liquid crystal cell includes a pair of substrates, such as glass plates, 73, 74, transparent electrodes 75, 76 on the respective substrates, electrical leads 77, 78 for connecting the respective electrodes to the drive circuitry for energization (application of a voltage) thereto, and liquid crystal material 79 in the space 80 between the substrates. A seal 81 seals the perimeter of the liquid crystal cell 65 to retain the liquid crystal material 79 in the space 80. The inner surfaces of the substrates 73, 74 and/or the electrodes 75, 76 have a surface treatment, for example, by rubbing, deposition, or some other technique, to align the liquid crystal material 79 with respect to those surfaces. In an exemplary case the alignment at one surface is relatively perpendicular to the alignment at the opposite surface. When the liquid crystal material 79 is of the nematic type (or is operationally nematic in that it has characteristics allowing it to operate like nematic liquid crystal), the liquid crystal aligns according to the treatment at the respective surfaces and will have a twist from one surface to the other. However, in response to application of suitable electric field input across the liquid crystal material, the liquid crystal material tends to align with the field. In the former case the liquid crystal material will rotate the plane of polarized light transmitted through it, and in the latter case the liquid crystal material will not affect the direction of polarization of the light transmitted through it, as is conventional.

In the indicator 11 the electrode segments 71 or the substrate 73 proximate those electrode segments also have surface treatments similar to that at the electrode 75 or rest of the substrate 73 surface as described above. Therefore, the liquid crystal material 79 in the space 80a between the electrode segment 71 and the electrode 76 also is in a twisted state in the absence of electric field or aligns with the electric field when a suitable voltage is applied between the respective electrode segment 71 and the electrode 76.

In operation of the indicator 1 1, light 90 is directed from the back 16 of the welding lens cartridge assembly 12 to the liquid crystal light shutter 53. The light is polarized by the polarizer 66 and is directed into the liquid crystal cell 65. At those areas where a suitable voltage is applied between a respective electrode segment 71 and the electrode 76, the electric field created there causes alignment of the liquid crystal material with the field so that no change in polarization direction occurs, and the light will be blocked from further transmission by the polarizer 64. However, where there is no electric field applied between a respective electrode segment 71 and the facing portion of the electrode 76, the liquid crystal material will remain twisted and will rotate the plane of polarization of the light transmitted therethrough. Accordingly, such light will be transmitted through the polarizer 64, will illuminate the reflective substrate 70 and respective one of the indicia thereof located in alignment with the then deenergized electrode segment 71. The light reflected by the reflective substrate 70 including the respective illuminated one of the indicia passes in a reverse direction back through the liquid crystal light shutter 53 for viewing by the user. More specifically, the reflected light is transmitted through the polarizer 64, the plane of polarization is rotated by the liquid crystal material in the space 80a, and the light is transmitted through the polarizer 66 for viewing. Similar operation is effected for the other portions of the indicator 11.

When the welding helmet 1 is positioned on the head of a user and welding is detected by the sensor 13, for example, and the lens 50 is driven to the dark state by the drive circuitry 14, electric field is supplied across all the liquid crystal material 79 in the liquid crystal cell 65, including that liquid crystal material not only in the space 80 but also that in the space 80a. Therefore, therefore, light blocking function will be provided by the entire liquid crystal shutter 53 including the integral indicator 11.

Another embodiment of an indicator 11a, which is similar to the indicator 11 described above, is illustrated in FIGS. 7 and 8. The indicator 11a is integral with a liquid crystal cell 65 that is part of a liquid crystal light shutter 53, which were described above. However, in the embodiment of FIG. 7, the indicator 11a is a transmissive one rather than a reflective one. More specifically, the indicator 11a includes electrode segments 71 that can be selectively energized from the drive circuitry 14 or not energized thereby to determine whether light 91 from the front 15 of the welding lens cartridge assembly will be transmitted through respective indicia 30. The indicia 30 may be painted, printed or otherwise formed on or applied to a substrate 70a shown in FIG. 8. Such substrate may be clear film, such as plastic, Mylar or some other material, and the indicia may be respective numbers, letters or symbols applied thereto and able to block light to provide information. Alternatively, the substrate 70a may be a light blocking material and the indicia may be transparent portions thereof.

The liquid crystal cell 65 and light shutter 53 of FIG. 7 operate in the manner described above, for example, with respect to FIG. 5. The indicator 11a is operable in response to voltage applied by the drive circuitry 14 to respective electrode segments 71 and electrode 76 (or not applying voltage thereto) to determine whether light 91 is transmitted through a respective one or more of the indicia 30 on the substrate 70a. For example, in the absence of electric field between an electrode segment 71 and electrode 76, light 91 is polarized by the polarizer 64, is transmitted through the substrate 73 and through the respective electrode segment 71, has the plane of polarization rotated by the twisted liquid crystal material 79, and then is transmitted through the electrode 76, substrate 74, polarizer 66 and finally through the effectively overlaying one of the indicia, thereby illuminating the indicia for viewing thereof. In response to application of voltage between an electrode segment 71 and electrode 76, though, the liquid crystal material 79 therebetween will align with the field and will not rotate the plane of polarization of polarized light transmitted therethrough; and, accordingly, light 91 is blocked by the polarizer 66 and will not illuminate the indicia 30.

It will be appreciated that other means may be used to form the respective indicia 30, such as, for example, electrode portions of the electrode segments 71, either in a light transmissive or light reflective type display arrangement, such as are described above and in the two U.S. Pat. Nos. 3,731,986 and 3,881,809 mentioned above.

In FIG. 9 the drive circuitry 14 is shown mounted on a circuit board 101 or other type of support. The power source 100 includes a battery 102, such as a lithium ion battery, or other electrical energy storage device. Additionally, the power source may include a solar cell 103 or other photoelectric type of device which is mounted in the welding lens cartridge assembly 12 for exposure to ambient light and/or to the welding light and in response to such light develops electrical energy to recharge the battery 102 and/or directly to supply electrical power to the drive circuitry 14. Electrical leads 104, 105 connect the solar cell 103 to electrically conductive traces (not shown) on the circuit board 101 for connection to the battery 102 and/or directly to the drive circuitry 14.

As shown in FIG. 9, the drive circuitry 14 is embodied in a single integrated circuit 14a. There may be additional resistors, capacitors, inductors, and/or other solid state or other components associated with the integrated circuit 14a which are mounted elsewhere on the circuit board 101 and connected to the integrated circuit 14a by conductive traces or the like, as is conventional. However, in an embodiment of the invention as much as possible of the drive circuitry 14 is embodied entirely within the integrated circuit 14a, for example, for compactness, ease of construction, etc. The circuitry 14 may be the same as or of the type disclosed in one or more of the above patents and applications.

The switches 31a, 31b, 31c may be mounted directly on the circuit board 101. Such switches may be a plurality of contacts above which a flexible membrane is positioned to be pressed toward respective contacts to urge a connection therebetween. Connections may be by flexing the respective contacts themselves or by flexible conductive material on the membrane itself.

Other types of switches alternatively may be used.

The drive circuitry 14 is connected to the birefringent mode liquid crystal cell 62 by respective electrical leads or other connections 110a, 110b, which are collectively designated 110 in the drawing of FIG. 4. The connections 72, 77, and 78 from the drive circuitry 14 to the twisted nematic liquid crystal cell 65, including the integral indicator 11, are included in a ribbon cable connector 111 or other multiconductor connector device. The connections 77, 78 are to the respective electrodes 75, 76; and a plurality of connections 72 are proved leading, respectively, to the respective electrode segments 71 do cause display of respective operating characteristics or conditions by the indicator 11.

Therefore, in response to the settings of the drive circuitry 14 under control of the respective switches 31, the drive circuitry may deliver appropriate voltages to respective electrode segments 71 causing the appropriate display of operating characteristics for the welding lens assembly 51 for viewing by the user. After having made the desired settings of the operating characteristics, the user may put on the welding helmet. While welding or other bright light condition is not detected by the sensor 13, the drive circuitry 14 would operate the welding lens 50 to the clear state. Upon detecting a light condition for which eye protection is desired, the sensor output to the drive circuitry 14 causes the drive circuitry to operate the welding lens 50 to dark condition according to the operating conditions or characteristics set in the circuitry by the switches 14.

Statement of Industrial Applicability

In view of the foregoing it will be appreciated that the present invention may be used to provide eye protection and a method of eye protection for a welder, to select operating characteristics of the welding lens assembly, and to display or to indicate those operating characteristics.

I claim:

1. A light transmission controlling device, comprising a liquid crystal shutter selectively operable to affect optical polarization and thereby to control transmission of light, said shutter comprising a plurality of shutter elements in optical series, and
an indicator integral with said shutter for indicating an operational characteristic of said shutter, said indicator being separately operable from said shutter.

2. The device of claim 1, said indicator being on one of said shutter elements.

3. The device of claim 1, said shutter comprising a birefringent liquid crystal cell and a twisted nematic liquid crystal cell in optical series.

4. The device of claim 1, further comprising an input polarizer for polarizing light incident on said shutter, and said indicator including means for causing selective transmission or blocking of some of such polarized light to provide a viewable output indicating such operational characteristic.

5. The device of claim 4, said shutter comprising a twisted nematic liquid crystal cell, and said indicator comprising a separately energizable portion of said twisted nematic liquid crystal cell for providing a viewable indicator output.

6. The device of claim 5, said separately energizable portion comprising a reflective liquid crystal display having respective segmented electrodes to present a discernible indication depending on the energization or not thereof.

7. The device of claim 5, said separately energizable portion comprising a transmissive liquid crystal display having respective segmented electrodes to present a discernible indication depending on the energization or not thereof.

8. The device of claim 5, said separately energizable portion comprising a reflective liquid crystal display and a viewable indicator that is selectively illuminated for viewing or not as a discernible indication depending on the energization or not thereof.

9. The device of claim 5, said separately energizable portion comprising a transmissive liquid crystal display and a viewable indicator that is selectively illuminated for viewing or not as a discernible indication depending on the energization or not thereof.

10. The device of claim 4, said indicator comprising a plurality of indicia for indicating respective operational characteristics.

11. The device of claim 1, said shutter comprising a relatively faster acting shutter and a relatively slower acting shutter in optical series, and further comprising a circuit for operating said shutters to block light transmission.

12. A light transmission controlling device comprising: a liquid crystal shutter selectively operable to affect optical polarization and thereby to control transmission of light, said shutter comprising a birefringent liquid crystal cell and a twisted nematic liquid crystal cell in optical series; and
an indicator integral with said shutter for indicating an operational characteristic of said shutter, said indicator being on said twisted nematic liquid crystal cell.

13. The device of claim 12, said indicator being operable to indicate operational characteristic of said birefringent liquid crystal cell.

14. A light transmission controlling device, comprising:
a liquid crystal shutter selectively operable to affect optical polarization and thereby to control transmission of light;
means for adjusting the shade darkness characteristic of said shutter;
an input polarizer for polarizing light incident on said shutter; and
an indicator integral with said shutter for indicating an operational characteristic of said shutter, said indicator being separately operable from said shutter and including a display for indicating the shade characteristic of the shutter, said indicator further including means for causing selective transmission or blocking of some of such polarized light to provide a viewable output indicating such operational characteristic.

15. A light transmission controlling device, comprising:
a liquid crystal shutter selectively operable to affect optical polarization and thereby to control transmission of light;
an adjuster for adjusting the sensitivity of said shutter;
an input polarizer for polarizing light incident on said shutter; and
an indicator integral with said shutter for indicating an operational characteristic of said shutter, said indicator being separately operable from said shutter and including a display for indicating the sensitivity of the shutter, said indicator further including means for causing selective transmission or blocking of some of such polarized light to provide a viewable output indicating such operational characteristic.

16. A light transmission controlling device, comprising:
a liquid crystal shutter selectively operable to affect optical polarization and thereby to control transmission of light, said shutter comprising an automatically darkening shutter, including means for operating the shutter to darken upon detection of a condition calling for a darkening;
an adjuster for adjusting delay of the shutter to return to a relatively transmissive state following termination of a condition calling for a darkened state;
an input polarizer for polarizing light incident on said shutter; and
an indicator integral with said shutter for indicating an operational characteristic thereof, said indicator including a display for indicating a characteristic of the delay, said indicator further including means for causing selective transmission or blocking of some of such polarized light to provide a viewable output indicating such operational characteristic.

17. A light transmission controlling device, comprising:
a liquid crystal shutter selectively operable to affect optical polarization and thereby to control transmission of light, said shutter comprising a relatively faster action shutter and a relatively slower acting shutter in optical series;
a circuit for operating said shutters to block light transmission, said circuit comprising drivers for driving said relatively faster acting shutter with power causing rapid switching to a substantially maximum light blocking condition, and maintaining that condition until said relatively slower acting shutter has switched to a substantially maximum light blocking condition; and
an indicator integral with said liquid crystal shutter for indicating an operational characteristic of said liquid crystal shutter.

18. The device of claim 17, said circuit further comprising means for reducing power for driving said relatively faster acting shutter after said relatively slower acting shutter has switched to a substantially maximum light blocking condition.

19. The device of claim 18, said relatively faster acting light shutter comprising a birefringent liquid crystal cell operable to cause light blocking over a range of darkness conditions as voltage of electric field applied thereto is varied over a range.

20. A light shutter having at least respective relatively dark and relatively clear states, comprising:
a light control device controllable to switch between respective relatively clear and dark states, said light control device comprising plural light control elements in optical series;
a circuit having respective operating modes for controlling operation of said light control device; and
an indicator on said light control device and responsive to said circuit for indicating said operating modes, said indicator being separately operable from said light control device.

21. The shutter of claim 20, said light control device comprising a twisted nematic liquid crystal cell including a pair of substrates, liquid crystal material between the substrates and electrodes for applying electric field to the liquid crystal material, and said indicator means comprising respective selectively operable portions of said twisted nematic liquid crystal cell to provide respective indicating outputs.

22. A light shutter having at least respective relatively dark and relatively clear states, comprising:
a light control device controllable to switch between respective relatively clear and dark states, said light control device comprising plural light control elements in optical series;
a circuit having respective operating modes for controlling operation of said light control device, and
an indicator on said light control device and responsive to said circuit for indicating said operating modes said indicator being on one of said light control elements and being separately operable from said light control elements to provide a viewable output when illuminated with light, and another of the light control elements when in the relatively dark state blocks light to or from the indicator thereby tending to preclude a viewable output therefrom.

23. A light shutter having at least respective relatively dark and relatively clear states, comprising:
a light control device controllable to switch between respective relatively clear and dark states;
a circuit having respective operating modes for controlling operation of said light control device, said circuit being operable to control at least two of shade, sensitivity and delay functions of the light shutter;
a selector for selecting respective settings of the functions, said selector comprising respective switches; and
an indicator on said light control device responsive to said circuit for indicating said operating modes, said indicator being separately operable from said light control device.

24. The shutter of claim 23, said switches comprising flexible switches.

25. The shutter of claim 24, said switches comprising membrane switches.

26. A light shutter having at least respective relatively dark and relatively clear states, comprising;
a light control device controllable to switch between respective relatively clear and dark states, said light control device comprising a relatively faster acting shutter and a relatively slower acting shutter in optical series;
a circuit having respective operating modes for controlling operation of said light control device, said circuit comprising drivers for driving said relatively faster acting shutter with power causing rapid switching to a substantially maximum light blocking condition, and maintaining that condition until said relatively slower acting shutter has switched to a substantially maximum light blocking condition; and an indicator on said light control device and responsive to said circuit for indicating said operating modes.

27. The shutter of claim 26, said circuit further comprising means for reducing power for driving said relatively faster acting shutter after said relatively slower acting shutter has switched to a substantially maximum light blocking condition, and said relatively faster acting light shutter comprising a birefringent liquid crystal cell operable to cause light blocking over a range of darkness conditions as voltage of electric field applied thereto is varied over a range.

28. An automatic welding lens system, comprising:

an input polarizer, a first light shutter operable selectively to affect polarization of incident polarized light, a first analyzer for transmitting or blocking light from the first light shutter depending on the polarization thereof, a second light shutter operable selectively to affect polarization of incident polarized light from the first analyzer, a second analyzer for transmitting or blocking light from the second light shutter depending on the polarization thereof, and an indicator integral with one of said light shutters for indicating an operational characteristic of said light shutters, said indicator being separately operable from said light shutters.

29. The system of claim 28, wherein one of said light shutters is operable to switch from one condition affecting or not affecting polarization faster than the other of said light shutters, and further comprising a circuit for energizing said shutters to switch them to light blocking mode, said circuit including means for changing operational parameters thereof, and said indicator being operable to indicate at least one of said operational parameters.

30. An automatic welding lens system, comprising;

an input polarizer, a first light shutter operable selectively to affect polarization of incident polarized light, a first analyzer for transmitting or blocking light from the first light shutter depending on the polarization of said first light shutter, a second light shutter operable selectively to affect polarization of incident polarized light from the first analyzer, a second analyzer for transmitting or blocking light from the second light shutter depending on the polarization of said second light shutter;

one of said light shutters being operable to switch from one condition affecting or not affecting polarization faster than the other of said light shutters;

a circuit for energizing said shutters to switch them to light blocking mode, said circuit including switches for changing operational parameters thereof, said operational parameters including at least two of shade, sensitivity, and delay functions of the system; and an indicator integral with one of said light shutters for indicating at least one of said operational parameters.

31. A liquid crystal optical device, comprising:

a light shutter for selectively controlling light transmission to a viewing area;

said light shutter including a pair of substrates, liquid crystal material between said respective substrates, said liquid crystal material being functional selectively to affect optical polarization characteristic of polarized light, electrodes associated with said respective substrates for selectively applying an electric field to liquid crystal material therebetween to change the characteristics of light transmission through a viewing portion of said light shutter;

at least one of said electrodes including an electrode portion that is separately operable from another portion thereof for selective operation to selectively reveal and conceal from view indicia representative of a characteristic of said light shutter.

32. The device of claim 31, further comprising a detector for detecting light, and a circuit responsive to said detector for supplying voltage to said electrodes to apply an electric field to liquid crystal material.

33. The device of claim 32, said circuit including a battery.

34. The device of claim 33, said circuit including a solar cell.

35. The device of claim 32, said circuit including a solar cell.

36. The device of claim 31, said light shutter comprising a plurality of liquid crystal cells in optical series, said electrode portion comprising an electrode portion of one of said liquid crystal cells, and further comprising an input polarizer for polarizing light incident on a first of said liquid crystal cells, a second polarizer between said liquid crystal cells and cooperative with said input polarizer and said first liquid crystal cell to transmit light or to block light transmission depending on the operative condition of said first liquid crystal cell, a second of said liquid crystal cells being positioned to receive light transmitted through said second polarizer, and a further polarizer for transmitting or blocking light depending on the operative condition of said second liquid crystal cell.

37. The device of claim 36, further comprising a further polarizer between said second polarizer and said second liquid crystal cell.

38. The device of claim 36, further comprising a wave plate between at least one of said polarizers and at least one of said liquid crystal cells for compensating for residual birefringence.

39. The device of claim 36, said first liquid crystal cell comprising a variable birefringence liquid crystal cell, a wave plate between said first polarizer and said variable birefringence liquid crystal cell for compensating for residual birefringence.

40. A welding lens assembly, comprising the liquid crystal optical device of claim 31, and further comprising a housing for holding therein the respective portions of the device.

41. A welding helmet, comprising a face shield portion and a lens assembly as set forth in claim 40.

42. The welding helmet of claim 41, further comprising a mount for mounting the welding helmet on the head of a person to place the shutter before the eyes of the person.

43. The device of claim 40, said light shutter and said indicator comprising a liquid crystal cell, and wherein operation of said light shutter and indicator is coordinated whereby when the shutter is in a light blocking mode the indicator also is in a light blocking mode.

44. The device of claim 40, further comprising a hot mirror optically upstream of the light shutter.

45. A liquid crystal optical device, comprising:

a light shutter for selectively controlling light transmission to a viewing area;

said light shutter including a pair of substrates, liquid crystal material between said respective substrates, said liquid crystal material being functional selectively to affect optical polarization characteristic of polarized light, electrodes associated with said respective substrates for selectively applying an electric field to liquid crystal material therebetween to change the characteristics of light transmission through a viewing portion of said light shutter;

at least one switch to select the operable mode of the shutter;

a detector for detecting light;

a circuit responsive to said detector for supplying voltage to said electrodes to apply an electric field to said liquid crystal material, said circuit including circuit portions responsive to operation of said switch to cycle through respective operational modes of the shutter; and at least one of said electrodes including an electrode portion that is separately operable from another portion thereof for selective operation to display for viewing indicia representative of a characteristic of said light shutter.

46. A liquid crystal optical device, comprising:

a light shutter for selectively controlling light transmission to a viewing area;

said light shutter including a pair of substrates, liquid crystal material between said respective substrates, said liquid crystal material being functional selectively to affect optical polarization characteristic of polarized light, electrodes associated with said respective substrates for selectively applying an electric field to liquid crystal material therebetween to change the characteristics of light transmission through a viewing portion of said light shutter;

a detector for detecting light;

a circuit responsive to said detector for supplying voltage to said electrodes to apply an electric field to said liquid crystal material, said circuit including an adjuster for adjusting the sensitivity to light characteristics of the light shutter in light blocking mode; and at least one of said electrodes including an electrode portion that is separately operable from another portion thereof for selective operation to display for viewing indicia representative of a characteristic of said light shutter, said electrode portion being operable to display indicia representing such sensitivity characteristic, and said circuit being operable to supply voltage to a respective part of said electrode portion to cause the display of indicia representing such sensitivity characteristic.

47. A liquid crystal optical device, comprising, a light shutter for selectively controlling light transmission to a viewing area, said light shutter including a pair of substrates, liquid crystal material between said respective substrates, said liquid crystal material being functional selectively to affect optical polarization characteristic of polarized light, electrodes associated with said respective substrates for selectively applying an electric field to liquid crystal material therebetween to change the characteristics of light transmission through a viewing portion of said light shutter, at least one of said electrodes including an electrode portion that is separately operable from another portion thereof for selective operation to display for viewing indicia representative of a characteristic of said light shutter;

an indicator for indicating an operative characteristic of said light shutter, said indicator including said electrode portion and said indicia, and said indicia comprising indicia mounted with respect to at least one of said substrates and viewable in response to light the transmission of which is controlled by liquid crystal material in proximity to said electrode portion.

48. The device of claim 47, said light shutter and said indicator comprising a liquid crystal cell, and wherein operation of said light shutter and indicator is coordinated whereby when the shutter is in a light blocking mode the indicator also is in a light blocking mode.

49. The device of claim 47, said light shutter including a primary viewing portion through which transmitted light may be seen through the light shutter, and wherein said electrode portion includes plural electrode portions respectively operable to provide light transmission through respective indicia to indicate the respective operative characteristic of said light shutter.

50. The device of claim 47, said light shutter including a primary viewing portion through which transmitted light may be seen through the light shutter, said indicator including a light reflecting portion, and said electrode portion including plural electrode portions respectively operable to provide light for reflection with respect to the indicia to cause illumination of respective indicia to indicate the respective operative characteristic of said light shutter.

51. The device of claim 31, further comprising a further light shutter in optical series with said light shutter, said further light shutter comprising a birefringent liquid crystal cell and said light shutter comprising a twisted nematic liquid crystal cell, and further comprising a circuit for applying voltage to said liquid crystal cells to drive said liquid crystal cells to light blocking mode, said birefringent liquid crystal cell being operable to achieve a light blocking mode faster than said twisted nematic liquid crystal cell.

52. A liquid crystal optical device, comprising:

a light shutter for selectively controlling light transmission to a viewing area;

said light shutter including a pair of substrates, liquid crystal material between said respective substrates, said liquid crystal material being functional selectively to affect optical polarization characteristic of polarized light, electrodes associated with said respective substrates for selectively applying an electric field to liquid crystal material therebetween to change the characteristics of light transmission through a viewing portion of said light shutter;

at least one of said electrodes including an electrode portion that is separately operable from another portion thereof for selective operation to display for viewing indicia representative of a characteristic of said light shutter;

a further light shutter in optical series with said light shutter, said further light shutter comprising a birefringent liquid crystal cell and said light shutter comprising a twisted nematic liquid crystal; and a circuit for applying voltage to said liquid crystal cells to drive said liquid crystal cells to light blocking mode, said birefringent liquid crystal cell being operable to achieve a light blocking mode faster than said twisted nematic liquid crystal cell; said circuit including a circuit portion initially providing energization to said birefringent liquid crystal cell to drive said birefringent liquid crystal cell to a first dark mode, simultaneously to drive said twisted nematic liquid crystal cell to dark mode and, after said twisted nematic liquid crystal cell has at least commenced being driven to dark mode, to reduce energization of said birefringent liquid crystal cell to hold a dark mode and to cooperate with said twisted nematic liquid crystal cell to achieve a dark mode for said light shutter.

53. A method of protecting the eyes of a welder using an automatic darkening welding lens assembly, comprising selecting an operating characteristic of the welding lens assembly, using a display portion of the welding lens assembly displaying such operating characteristic, placing a viewing portion of the welding lens assembly before the eyes of the welder to provide a light shuttering operation for eye protection, and darkening the display portion of the welding lens assembly when the viewing portion is darkened to protect the eyes of the welder.

54. The method of claim 53, said placing comprising placing an optical series of liquid crystal cells between the eyes of the welder and a welding site.

55. The method of claim 54, said placing comprising placing a twisted nematic liquid crystal cell and a birefringent liquid crystal cell between the eyes of the welder and the welding site.

56. The method of claim 55, said displaying comprising displaying simultaneously plural operating conditions of the welding lens assembly.

57. The method of claim 54, said selecting comprising selecting operation of the liquid crystal cells by pressing membrane switches to cycle through respective operational modes of a drive circuit for the welding lens assembly.

58. A light shutter for a welding helmet, said light shutter comprising:

a light control device selectively operable between relatively clear and relatively dark states, a control circuit having respective operating modes for controlling operation of said light control device between said relatively clear and relatively dark states, and an indicator on said light control device for indicating an operational characteristic of said light control device, said indicator being separately operable and separately viewable from said light control device.

59. The light shutter of claim 58 wherein said indicator is integral with said light control device.

60. The light shutter of claim 59 wherein said indicator and said light control device are arranged in an overlapping configuration so that operation of said light control device into a relatively dark state obscures said indicator.

* * * * *